(12) United States Patent
Matahira et al.

(10) Patent No.: US 6,919,306 B2
(45) Date of Patent: Jul. 19, 2005

(54) METHOD OF SKIN CARE

(75) Inventors: Yoshiharu Matahira, Shizuoka-ken (JP); Michiko Saito, Shizuoka-ken (JP); Nobuyuki Sugita, Shizuoka-ken (JP)

(73) Assignee: Yaizu Suisankagaku Industry Co. Ltd., Yaizu (JP)

(*) Notice: Subject to any disclaimer, the term of this patent is extended or adjusted under 35 U.S.C. 154(b) by 0 days.

(21) Appl. No.: 10/076,686

(22) Filed: Feb. 14, 2002

(65) Prior Publication Data

US 2003/0022842 A1 Jan. 30, 2003

Related U.S. Application Data

(63) Continuation-in-part of application No. 09/558,487, filed on Apr. 25, 2000, now abandoned.

(30) Foreign Application Priority Data

Aug. 9, 1999 (JP) .......................................... 11-225245

(51) Int. Cl.$^7$ ........................ A61K 31/70; A61K 38/00
(52) U.S. Cl. ............................. 514/2; 514/62; 514/878; 426/573; 426/583; 426/589; 426/590; 426/655; 426/657; 426/658; 426/660; 424/439; 424/440; 424/451; 424/464; 424/489
(58) Field of Search ................. 424/400, 421, 424/439, 489, 78.01; 514/474, 777, 42, 62

(56) References Cited

U.S. PATENT DOCUMENTS

| | | | | |
|---|---|---|---|---|
| 5,217,962 A | * | 6/1993 | Burton et al. .................. 514/62 |
| 5,804,594 A | * | 9/1998 | Murad .......................... 514/474 |
| 5,981,510 A | * | 11/1999 | Fujiwara et al. ............... 514/62 |
| 5,998,173 A | * | 12/1999 | Haynes et al. ................. 435/84 |
| 6,242,431 B1 | | 6/2001 | Fujiwara et al. | |

FOREIGN PATENT DOCUMENTS

| | | |
|---|---|---|
| EP | 1 075 836 A2 | 2/2001 |
| JP | 62-198366 A | 9/1987 |
| JP | 05-093000 | 4/1993 |
| JP | 05-125100 | 5/1993 |
| JP | 08165243 A | 6/1996 |
| JP | 08-173091 | 7/1996 |
| JP | 09-098739 | 4/1997 |
| JP | 10-000070 | 1/1998 |
| JP | 10-165138 | 6/1998 |
| JP | 11-113530 | 4/1999 |
| JP | 2000-050842 A | 2/2000 |
| JP | 2000-281696 | 10/2000 |
| JP | 2001-048789 | 1/2001 |
| JP | 00108263 | 2/2001 |
| JP | 2001-200000 | 7/2001 |
| KR | 2001-0029674 | 4/2001 |

OTHER PUBLICATIONS

Suzuki et al., JP408165243A, Anti–inflammatory Agent, Jun 25, 1996, abstract.

Matsuura et al., JP 01268618, Oct. 26, 1989, Cosmetic, abstract.*

The Government of the Hong Kong S.A.R. Gazette Dated 2$^{nd}$ Nov. 2001, No. 6 to Gazette No. 44/2001 of JP 1034648, Aug. 9, 1999, "Skin Care Agent, and Health and Beauty Care Food".

* cited by examiner

Primary Examiner—Frederick F Krass
(74) Attorney, Agent, or Firm—Frishauf, Holtz, Goodman & Chick, P.C.

(57) ABSTRACT

The present invention provides a method for skin care by orally administering a skin care agent comprising an ingestible carrier and natural-type N-acetylglucosamine obtainable by hydrolysis of chitin with an acid, an enzyme, or an acid and an enzyme, wherein the natural-type N-acetylglucosamine is contained in an amount of from 0.1 to 99.9% by weight, by which the moisture and tension of skin can be improved and the rough skin and fine wrinkles can be prevented or ameliorated. The skin care agent may be a skin care agent containing chitinoligosaccharide in an amount of from 0.1 to 20% by weight and natural-type N-acetylglucosamine in an amount of from 0.1 to 99.9% by weight; or a skin care agent containing collagen peptide in an amount of from 0.1 to 99.9% by weight and natural-type N-acetylglucosamine in an amount of from 0.1 to 99.9% by weight.

13 Claims, 1 Drawing Sheet

METHOD OF SKIN CARE

This is a continuation-in-part application of U.S. application Ser. No. 09/558,487 filed Apr. 25, 2000 now abandoned.

FIELD OF THE INVENTION

The present invention relates to a method for skin care (or a method for promoting skin-beautification) which improves moisture and tension of skin and promotes prevention and amelioration of e.g. rough skin and fine wrinkles by orally ingesting a skin care agent containing a natural-type N-acetylglucosamine).

BACKGROUND OF THE INVENTION

Acidic mucopolysaccharides such as hyaluronic acid or chondroitin sulfate have a high water retention, bond to collagen which serves as a column of intercellular substance matrix, and are mostly distributed in, for example, connective tissues, cartilaginous tissues and skin tissues, thereby being useful for keeping functions and forms of cells.

In the skin tissues, the acidic mucopolysaccharides, collagen, etc. mostly exist in corium layer and take a large part in water retention and resilience of skin. It is known that when the amounts thereof decrease due to aging or the like, the water retention and resilience of skin will be lost, thereby causing rough skin, fine wrinkles, etc.

Accordingly, in order to prevent and ameliorate the rough skin and fine wrinkles, it is important to maintain the moisture and tension of skin. For this purpose, cosmetics to which various components having effects for maintaining the moisture retention and resilience of skin are incorporated, are commercially available. As such components, for example, the mucopolysaccharides such as hyaluronic acid, chondroitin sulfate and collagen, low molecular weight saccharides such as trehalose and sorbitol, vitamins, amino acid derivatives, ceramide, α-orizanol, and fats and oils such as refined camellia oil, may be mentioned. Particularly recently, components derived from natural substances having a high safety are likely to be regarded as more worthy.

Further, many health and beauty care foods have been developed which enhance the above-mentioned effects by oral ingestion. For example, health and beauty care foods comprising nucleic acid and mucopolysaccharides which contain hyaluronic acid, chondroitin sulfate and collagen (Japanese Unexamined Patent Publication No. 10-165138), processed foods comprising as a main component a mixture of at least two food materials of active oxygen elimination factors, antiallergic factors, factors for improving e.g. skin, and antioxidation factors (Japanese Unexamined Patent Publication No. 10-70), foods comprising conchiolin or its processed product (Japanese Unexamined Patent Publication No. 8-173091), health foods comprising conjugated mucopolysaccharide wherein a mucopolysaccharide and peptide are bonded (Japanese Unexamined Patent Publication No. 9-98739), and health foods containing ceramide (Japanese Unexamined Patent Publication No. 11-113530), may be mentioned.

On the other hand, natural-type N-acetylglucosamine is one of natural aminosugars obtainable by decomposing a high molecular weight polysaccharide chitin contained in shells of crustacea such as crab and shrimp or lobster, and is a white crystalline powder having a good sweetness of about a half of sugar and being less in moisture absorption. Natural-type N-acetylglucosamine is also contained in milk in a free state in an amount of about 10 mg/100 ml, and exists universally in living organisms as constituting units of sugar chains of mucopolysaccharide, glycoprotein and glucolipide. Natural-type N-acetylglucosamine is usually produced from glucose as a starting material by metabolism in living organisms, and one of living organism components having a high safety to human being. As physiological actions of natural-type N-acetylglucosamine, amelioration of arthritis symptom, propagation-accelerating effect of Lactobacillus vifidus, and the like, have been known.

However, since hyaluronic acid, chondroitin sulfate, collagen and the like are high molecular weight compounds and hardly absorbed only by coating them on the skin like cosmetics, these components are used for the purpose of improving the water retention of skin surface when these are used for cosmetics. This is true for most of the above-mentioned other components. Further, if the high molecular weight compounds such as hyaluronic acid, chondroitin sulfate and collagen, are orally ingested, there is a problem in digestion and absorption and their effects are not necessarily satisfactory.

SUMMARY OF THE INVENTION

Accordingly, it is an object of the present invention to provide a method of skin care which has an action such as improvement of moisture and tension of skin and prevention and amelioration of, e.g., rough skin and fine wrinkles by orally ingesting a specific skin care agent.

The present inventors have intensively studied to accomplish the above object, and as a result, have found that natural-type N-acetylglucosamine orally ingested is rapidly absorbed from intestine and reaches cutaneous layer, and in the cutaneous layer, it promotes biosynthesis of mucopolysaccharides such as hyaluronic acid, and accomplished the present invention.

Namely, the present invention provides a method of skin care for a human, which comprises orally administering a skin care agent comprising an ingestible carrier and natural-type N-acetylglucosamine obtainable by hydrolysis of chitin with an acid, an enzyme, or an acid and an enzyme, wherein the natural-type N-acetylglucosamine is contained in an amount of from 0.1 to 99.9% by weight.

According to the present invention wherein natural-type N-acetylglucosamine is incorporated in the skin care agent, when it is ingested, most of the natural-type N-acetylglucosamine are rapidly absorbed and a part thereof is utilized as a starting material of mucopolysaccharides such as hyaluronic acid or chondroitin sulfate, whereby the moisture and tension of skin can be improved and the rough skin and fine wrinkles can be prevented and ameliorated.

Further, the natural-type N-acetylglucosamine has no risk such that a solvent or the like may remain, and is safe to human bodies and can be ingested without risk.

In a preferred embodiment of the present invention, the skin care agent comprises chitinoligosaccharide and the above-mentioned natural-type N-acetylglucosamine, wherein the chitinoligosaccharide is contained in an amount of from 0.1 to 20% by weight and the natural-type N-acetylglucosamine is contained in an amount of from 0.1 to 99% by weight. The skin care agent may further contain an ingestible carrier, as the case requires.

Chitinoligosaccharide has been reported to have a diabetes-preventing effect (U.S. Pat. No. 5,981,510), effects for preventing or ameliorating liver function failure (U.S. Pat. No. 6,242,431), and further immunity-activating effect and blood glucose level-reducing effect. Further, health promotion effect can be given by addition of chitinoligosaccharide.

Further, a mixture of natural-type N-acetylglucosamine and chitinoligosaccharide can be obtained readily by hydrolysis of chitin with an acid and an enzyme, and thus the cost of starting materials can be reduced.

In another preferred embodiment of the present invention, the skin care agent comprises collagen peptide and the above-mentioned natural-type N-acetylglucosamine, wherein the collagen peptide is contained in an amount of from 0.1 to 99.9% by weight and the natural-type N-acetylglucosamine is contained in an amount of from 0.1 to 99.9% by weight. The skin care agent may further contain an ingestible carrier, if the case requires.

Collagen peptide is digested and absorbed easily as compared with collagen, and has effects for accelerating metabolism of skin and keeping tension and moisture of skin. Accordingly, by using natural-type N-acetylglucosamine and collagen peptide in combination, skin-beautification promoting effect can further be enhanced.

DESCRIPTION OF THE PREFERRED EMBODIMENTS

Figure 1:
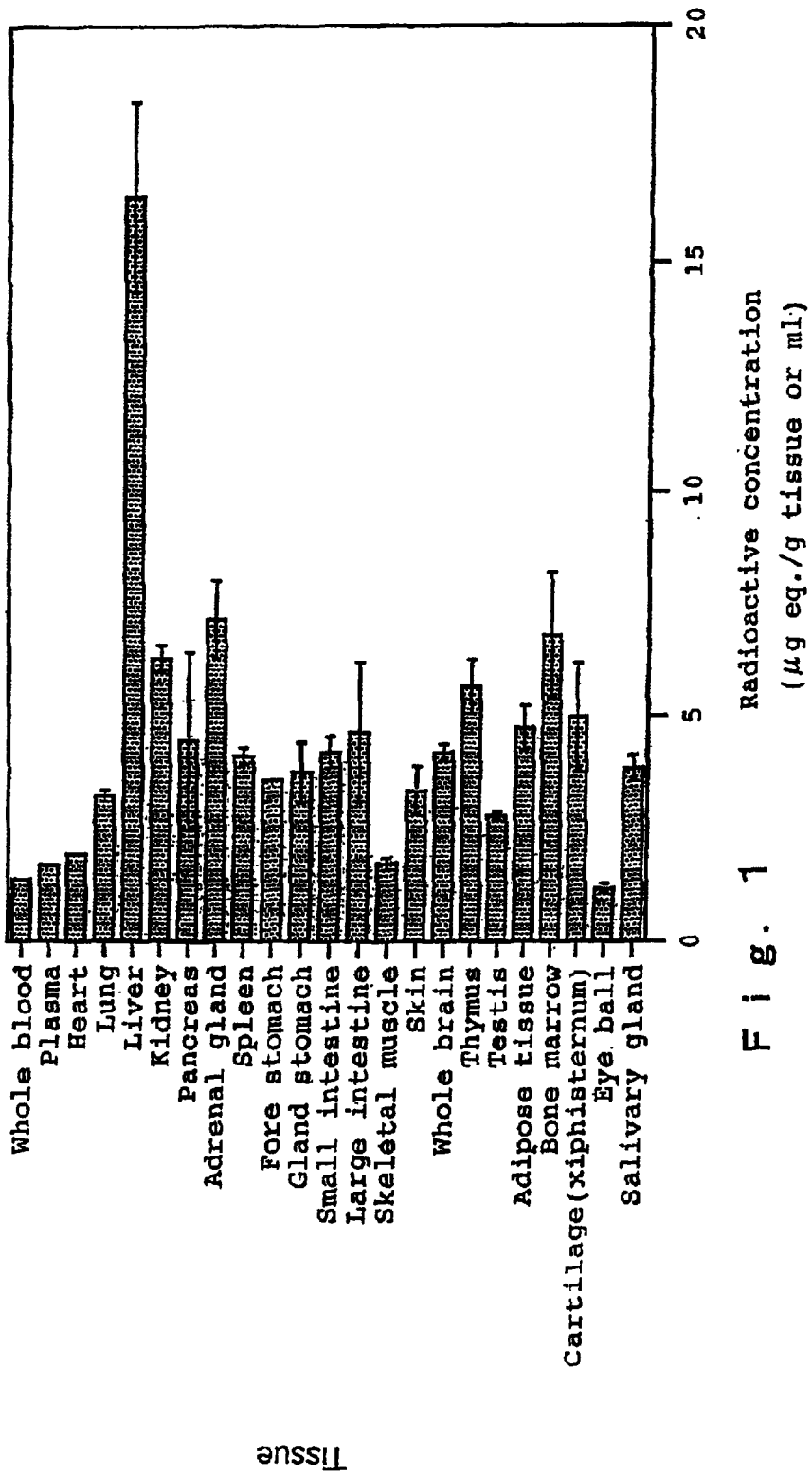
FIG. 1 is a graph showing the tissue distribution of radioactivity after administration of radioactivity-labeled natural-type N-acetylglucosamine.

Hereinafter, the present invention will be described in further detail with reference to preferred embodiments.

In the present invention, as natural-type N-acetylglucosamine, a NAG obtainable by hydrolysis of natural polysaccharide chitins derived from shells of crustacea such as crab and shrimp or lobster with an acid and/or an enzyme (natural-type NAG) is used.

A NAG obtainable by acetylation by chemical synthesis of a D-glucosamine chlorate which is obtainable by complete acidic hydrolysis of chitin (chemically synthesized NAG) has also been known. However, the chemically synthesized NAG has a risk such that since a solvent such as methanol is used, the solvent may remain. Further, not only amino group but also hydroxyl group is acetylated, whereby O-acetylated product may be formed. On the other hand, in the present invention, by using the natural-type N-acetylglucosamine, a highly safe product is provided.

The natural-type N-acetylglucosamine (hereinafter sometime simply referred to as "NAG") may be produced by carrying out hydrolysis of chitin with an acid and/or an enzyme, and as the case requires, selectively collecting NAG from this hydrolyzate by a means such as a separating membrane or an ion exchange resin.

In a preferred example of methods for producing the natural-type N-acetylglucosamine, firstly, chitin is partially hydrolyzed with an acid, and the hydrolyzed liquor is neutralized, and then deionized by electodyalysis with an ion exchange membrane, to prepare a mixture of NAG and chitinoligosaccharide (N-acetylchitooligosaccharide).

Then, chitinase is allowed to react to this mixture to further decompose the chitinoligosaccharide to prepare NAG. Further, as the case requires, undecomposed chitinoligosaccharide is removed by treatment with activated carbon, and NAG is selectively collected by treatment with an ion exchange resin, to obtain a highly purified natural-type NAG.

The purification may be carried out with a separating membrane such as a RO membrane or a NF membrane, in addition to the treatment with an ion exchange resin. As the separating membrane, ones having a salt-preventing rate of from 10 to 90% may preferably be used.

The natural-type NAG and the chemically synthesized NAG are completely same in the molecular formula and stereostructure, but differ in the contents of isotope of carbon (carbon 14) due to the difference in the origin of carbon of an acetyl group by the difference in the production methods.

Namely, carbon dioxide present in the upper atmosphere is taken in phytoplankton and transferred to living organisms such as crab and shrimp or lobster by food chain, resulting in the formation of the natural-type N-acetylglucosamine. Accordingly, the natural-type N-acetylglucosamine contains an isotope of carbon 14, although in a minute amount. On the other hand, no carbon 14 remains in the carbon of acetic anhydride produced by fossil fuel which has been existing in underground for as long as a few tends million years.

Accordingly, by the content of carbon 14, it is distinguishable whether NAG is natural-type NAG or chemically synthesized NAG. For example, an acetyl group of NAG is cleaved and collected as sodium acetate, and then its dating is calculated by mass spectrometry with an accelerator based on the half life period of carbon 14 as a standard. As a result, for example, if the dating result is the present time, this NAG is a natural-type NAG, and if about 40,000 years earlier, a chemically synthesized NAG.

In the present invention, natural-type NAG is contained as an active ingredient in the skin care agent in an amount of preferably from 0.1 to 99.9% by weight, more preferably from 1 to 50% by weight, most preferably from 35 to 50% by weight.

Further, in the present invention, a mixture of the natural-type NAG and chitinoligosaccharide may be used as an active ingredient. In this case, it is preferred to incorporate them so that the content of the natural-type NAG is from 0.1 to 99.9% by weight, and the content of chitinoligosaccharide is from 0.1 to 20% by weight in the skin care agent.

Furthermore, in the present invention, the natural-type NAG and collagen peptide may be used as active ingredients. In this case, it is preferred to incorporate them so that the content of the natural-type NAG is from 0.1 to 99.9% by weight, and the content of collagen peptide is from 0.1 to 99.9% by weight in the skin care agent.

In this case, as the collagen peptide, ones obtained by extracting collagen from skin or its adjacent portion, or bone or its adjacent portion of fishes, followed by enzymolysis and reverse osmosis membrane treatment, which contain at most 1.0% by weight of free amino acid and at most 2 ppm of arsenic, may preferably be used. Further, ones having number average molecular weight of from 1,000 to 10,000 may more preferably be used.

The collagen peptide extracted from skin or its adjacent portion, or bone or its adjacent portion of fishes, can safely be used, as compared with materials from dairy farmers, since it is free from infection of diseases such as bovine spongiform encephalopathy, and foot and mouth disease of pig or hog.

Further, by reducing the free amino acid content, the smelling of fishes can be reduced, and by reducing the arsenic content, safety can further be improved.

Moreover, by adjusting the number average molecular weight to a range of from 1,000 to 10,000, the viscosity of its aqueous solution can be made low and its handling efficiency can be improved.

The collagen peptide used in the present invention is produced by a step of preparing an extract containing collagen from skin or its adjacent portion, or bone or its adjacent portion of fishes, a step of enzymolysis of the extract, and a step of concentration and purification of the enzymolysis product of the extract with a reverse osmosis membrane.

In this case, it is preferred to insert a step of decoloring and deodorizing the extract containing collagen and its enzymolysis product. Further, it is preferred to use a reverse osmosis membrane having a salt preventing rate of from 10 to 50%.

The skin care agent of the present invention preferably contains other components which have already been recognized to have a skin-beautification (or skin care) effect, for example, collagen, chondroitin sulfate, hyaluronic acid, vitamin C, vitamin B group, trehalose and ceramide. Among them, it is preferred to contain at least one selected from collagen, chondroitin sulfate and vitamin C.

In the present invention, the uptake of the natural-type NAG is preferably from 0.1 to 15 g, more preferably from 0.3 to 5 g, most preferably from 0.5 to 1.5 g per day for adult. If the uptake of the natural-type NAG is less than 0.1 g, the skin-beautification effect can not be expected, such being undesirable. Further, if the uptake of the natural-type NAG exceeds 15 g, there is a possibility of symptom such as pasty stool or diarrhea, such being undesirable. In this connection, as shown in the test examples as described below, safety is confirmed even if the natural-type NAG is orally administered in an amount of 5 g per kg of body weight of rat.

In the present invention, when the natural-type NAG and chitinoligosaccharide are used in combination, the intake of chitinoligosaccharide is preferably from 0.01 to 2 g, more preferably from 0.05 to 1.5 g, most preferably from 0.5 to 1.0 g, per day for adult.

In the present invention, when the natural-type NAG and collagen peptide are used in combination, the intake of collagen peptide is preferably from 0.1 to 10 g, more preferably from 0.2 to 8.0 g, most preferably from 0.5 to 5.0 g, per day for adult.

The skin care agent used in the present invention is preferably formed in the shape of tablets, capsules, powder, granules, liquid or past.

For example, the tablets are obtained by uniformly mixing the natural-type NAG, the components having skin-beautification effect together with excipients such as lactose and starch, and tabletting the mixture by a pressure-type tabletting machine.

The powder and granules are obtainable by using the above mixture as it is or subjecting it to granulation.

The capsules are obtainable by uniformly dispersing the natural-type NAG and the components having skin-beautification effect in fats and oils such as safflower oil, and then adding e.g. beeswax thereto to appropriately adjust the viscosity of slurry, followed by filling it into a soft capsule made of gelatin and glycerol as main components of encapsulating materials by a soft capsule filling machine.

Further, the natural-type NAG has a solubility of 32% by weight in water of 25° C. and is confirmed not to show coloration or decomposition even if heat treated with pH of 2 to 8 at 100° C. for 1 hour, and has a stability in usual food processing without problem at all, whereby the natural-type NAG can be added as a food material to foods. In the present invention, as a carrier for the skin care agent, foods such as confectioneries, powdered soups, dairy products and beverages, may, for example, be mentioned. As such foods, specifically, gum, candies, tabletted confectioneries, chocolate, jelly, cookies, snacks, corn potage soup, consomme soup, milk, pudding, yogurt, ice cream, lactic acid beverages, alcohol beverages, vitamin beverages, mineral beverages, coffee beverages, near water, nutrition drinks, and the like, may be mentioned.

When the skin care agent of the present invention is ingested as food, the natural-type NAG should preferably be contained in an amount of from 0.1 to 15 g, more preferably from 0.3 to 5 g, per meal.

When the natural-type NAG and chitinoligosaccharide are used in combination, chitinoligosaccharide is contained in an amount of preferably from 0.01 to 2 g, more preferably from 0.05 to 1.5 g, most preferably from 0.5 to 1.0 g, per meal or per portion of food.

When the natural-type NAG and collagen peptide are used in combination, collagen peptide is contained in an amount of preferably from 0.1 to 10 g, more preferably from 0.2 to 8.0 g, most preferably from 0.5 to 5.0 g, per meal or per portion of food.

Hereinafter, the present invention will be described in further detail with reference to examples. In the following examples, "%" means "% by weight", unless otherwise specifically described.

PREPARATION EXAMPLE 1

Preparation of Natural-type NAG 4 kg of chitin was added to 12 liters of conc. hydrochloric acid and partial hydrolysis was carried out while stirring at 40° C. for 3 hours. After the completion of the hydrolysis, this was diluted with water of the same volume, and neutralized to pH 5.0 with a 25% sodium hydroxide solution. 500 g of activated carbon was added to this neutralized solution, and stirring was carried out for 30 minutes for decoloring, and then filtration was carried out with a filter paper and insolubles and the activated carbon were removed to obtain 42 liters of a filtrate. This filtrate was subjected to deionization by an ion exchange membrane electrodialyser to obtain about 20 liters of the deionized liquid. This deionized liquid contained about 1.7 kg of chitinoligosaccharide. To this chitinoligosaccharide-containing solution, 50,000 units of chitinase (manufactured by Sigma Co.) was added, and then an enzyme was permitted to react thereto at 45° C. for 50 hours to decompose the chitinoligosaccharide and form natural-type NAG. After deactivation of the enzyme by heating, undecomposed chitinoligosaccharide was removed by treatment with 1 kg of activated carbon, and then treatment with an ion exchange resin was carried out, followed by condensation and freeze drying to obtain 1.35 kg of natural-type NAG having a purity of 99.5%.

PREPARATION EXAMPLE 2

Preparation of a Composition of Natural-type NAG and Chitinoligosaccharide

In PREPARATION EXAMPLE 1, after the chitinoligosaccharide was decomposed by the addition of chitinase, the decomposed product was as it was concentrated and freeze dried to obtain a composition of natural-type NAG and chitinoligosaccharide, containing 98.5% of NAG and 1.5% of chitinoligosaccharide.

PREPARATION EXAMPLE 3

Preparation of Collagen Peptide 24 liters of water was added to 12 kg of a preliminarily decalcified cod bone and its adjacent portion to conduct extraction under heating (95° C., 3 hours). After cooling, this extract was subjected to separation into solid and liquor with a wire net of 16 mesh, and then filtrated with a filter paper to obtain 30 liters of extract liquor containing collagen (Brix 6.0%).

This extract liquor was adjusted to pH 7.0 and heated to 60° C. 3.6 g of a preparation of protease (tradename: "Protease N", manufactured by Amano Enzyme, hereinafter the same applies) was added thereto, and enzymatic reaction was carried out for 60 minutes. To this enzymatic reaction liquor, 360 g of activated carbon (tradename: "Taiko SW50", manufactured by Nimura Kagaku, hereinafter the same applies) was added. This liquor was heated to 80° C. for 15 minutes, and then cooled, followed by filtration with a filter paper to obtain 25 liters of a filtrate (Brix 6.0%).

This filtrate was subjected to treatment with a membrane using a reverse osmosis membrane having a salt-preventing rate of 10% (tradename: "NTR-7410", manufactured by Nitto Denko Corp.), to obtain 11 liters of a concentrated liquor (Brix 12.0%). This concentrated liquor was spray dried to obtain 900 g of a white collagen peptide powder.

With respect to this collagen peptide powder, free amino acid content, arsenic content, viscosity and number average molecular weight were measured by the following methods.

Free amino acid content: HPLC method,

Arsenic content: atomic absorption spectroscopy,

Viscosity: a 10 wt % aqueous solution of a sample was prepared and then the viscosity at 20° C. was measured by a B-type rotation viscometer, Number average molecular weight: HPLC method As the results, the free amino acid content was 0.6%, the arsenic content was at most 2 ppm, the viscosity was 24 cps and the number average molecular weight was 2,400. Further, organoleptic tests were conducted and the taste and odor were good.

TEST EXAMPLE 1

Acute Toxic Test of NAG

To each of five males and five females of Wister rats (SPF), NAG was given by a single oral administration in an amount of 5,000 mg per kg of body weight. After the administration, these rats were bred for 14 days and observed, and no death was recognized. It was also recognized that the 50% lethal dose ($LD_{50}$) to the rats was at least 5,000 mg per kg of body weight.

TEST EXAMPLE 2

NAG Kinetics Study

A mixture of $^{14}C$ labelled NAG (1 st-position carbon atom-labelled product: manufactured by Amasham Life Science Co.) and unlabelled NAG (the one prepared in PREPARATION EXAMPLE 1) was given to rats by single forced oral administration (250 mg/kg of body weight) for in vivo kinetics study. After the administration, the NAG was rapidly absorbed and the average concentration of radioactivity in blood reached the maximum value 4 hours after the administration and showed prompt attenuation until 24 hours later. About 60% of the administered NAG was utilized as an energy source and excreted as $CO_2$ to expiration. Further, about 20% was excreted to urine and stool. With respect to the residual of about 20%, the image analysis by autoradiography and the results of radioactive concentration analysis of the respective tissues as shown in FIG. 1, suggest that the residual of about 20% was widely transferred to e.g. cartilaginous tissues and fatty tissues in the living organism, and utilized as constituting substances of the living organism.

TEST EXAMPLE 3

Influential Test of NAG on Skin

Using hairless rats, influence of orally administered NAG on the content of hyaluronic acid in skin was tested. The NAG prepared in PREPARATION EXAMPLE 1 was mixed to a basic feed (Solid feed MF, manufactured by Oriental Kobo Kogyo Kabushiki Kaisha), and rats were permitted to freely ingest the mixture so that the substantial administered amount of NAG would be 0, 20 or 200 mg/kg of body weight/day. Administration was continued for 4 weeks from 9 week instar to 13 week instar, and the hyaluronic acid amounts in skin layer were measured separately for epidermis and corium. In this connection, the measurement of the hyaluronic acid was carried out in accordance with a hyaluronic acid measurement kit (manufactured by Chugai Shindanyaku Co.). The results are shown in Table 1.

TABLE 1

| Ingested amount of NAG | Hyaluronic acid content ($\mu g/g$ dried tissue) | |
| --- | --- | --- |
| (mg/kg/day) | Epidermis | Corium |
| 0 | 31.25 | 462.7 |
| 20 | 33.77 | 506.6 |
| 200 | 35.09 | 549.8 |

As is evident from Table 1, it was confirmed that the hyaluronic acid contents in the epidermis and corium tend to increase together in proportion to the administered amounts of NAG.

TEST EXAMPLE 4

Influential Test of NAG on Skin 20 adult female volunteers of age ranging from 25 to 45 years old were classified into two groups i.e. a test group and a control group. They were asked to take tablets prepared similarly as in Example 1 as described below at a rate of 5 tablets per shot, twice a day (NAG ingestion amount per day: 1.2 g) together with water, provided that the tablets for the control group were prepared by using lactose as a placebo instead of NAG. The test period was 60 days, and after the completion of test, they were questioned about skin conditions and the like by questionnaires. No particular restriction was made with respect to diet, makeup and the like during the test period. The results are shown in Table 2.

TABLE 2

| Items of questionnaires | Test region | Placebo region |
| --- | --- | --- |
| Feel moistness in skin | 7 | 2 |
| Feel tension in skin | 6 | 2 |
| Fine wrinkles decreased | 5 | 1 |
| Skin conditions improved as a whole | 8 | 2 |
| Skin conditions worsened as a whole | 0 | 1 |
| No change (including unidentified) | 2 | 5 |

As is evident from Table 2, as compared with the placebo region, many persons of the test region felt that the skin conditions were improved as a whole, for example, feeling moistness or tension in the skin as compared with the conditions before the start of the test. Accordingly, the skin-beautification effect of NAG was recognized.

TEST EXAMPLE 5

To 22 females usually having a tendency of xeroderma and rough skin (average age: 25.5±10.7), a double blind long-term ingestion study was carried out in the following manners provided that a placebo of NAG-containing tablets were given to a control group.

Subject Group

NAG-containing tablets-administered group (NAG group, n=11): Tablets prepared similarly as in Example 1 as described below (NAG amount: 200 mg/tablet), were ingested at a rate of 5 tablets/day (NAG 1,000 mg/day, as a daily dose).

Placebo-administered group (Placebo group, n=11): Tablets prepared similarly provided that lactose was used instead of NAG, were ingested at a rate of 5 tablets/day.

Ingestion Period and Inspection Period

The ingestion period was 8 weeks in each group. The inspection was in principle carried out just before the start of ingestion, 4 weeks after the start of ingestion, and just before the completion of ingestion (8 weeks after the start of ingestion).

Inspection Process (1) Dermatologic Examination and Doctor's Questions

In the observation of whole body, 4 ranks evaluation (0: no symptom, 1: slight, 2: medium, 3: severe) was conducted with respect to pruritus, desiccation, flushing, erosion, desquamation, papula, vesicle and tumefaction. In the observation of face, 4 ranks evaluation was similarly conducted with respect to cosmetic dermatitis, desiccation, flushing and spread of cosmetics. Further, amelioration of general symptom including the observations of the whole body and face, was evaluated as a general observation. These evaluations were conducted by a plurality of doctors designated by Japan Dermatologic Science Society. The results are shown in Table 3 (average value of each score of each group).

TABLE 3

| | | Number of sympto- matic persons | Before ingest- ion | After 4 weeks | After 8 weeks |
|---|---|---|---|---|---|
| | | NAG group (n = 11) | | | |
| Face | Cosmetic dermatitis | 3 | 1.00 | 1.00 | 1.33 |
| | Dessication | 11 | 2.00 | 1.18** | 1.00* |
| | Flushing | 10 | 1.80 | 1.10* | 1.10* |
| | Spread of cosmetics | 6 | 1.83 | 1.33 | 0.83* |
| Whole body | Pruritus | 10 | 1.40 | 0.90 | 0.60 |
| | Dessication | 11 | 2.09 | 1.36* | 1.00* |
| | Flushing | 5 | 1.40 | 0.80 | 0.40 |
| | Erosion | 1 | 2.00 | 1.00 | 0.00 |
| | Desquamation | 3 | 1.33 | 1.33 | 1.00 |
| | Papula | 2 | 1.00 | 1.50 | 1.50 |
| | Vesicle | 1 | 1.00 | 2.00 | 2.00 |
| General observation | | 11 | 1.82 | 1.27* | 1.09* |
| | | NAG group (n = 11) | | | |
| Face | Cosmetic dermatitis | 0 | — | — | — |
| | Dessication | 11 | 2.00 | 1.73 | 1.55 |
| | Flushing | 10 | 1.60 | 1.40 | 1.30 |
| | Spread of cosmetics | 6 | 2.17 | 1.50 | 1.67 |
| Whole body | Pruritus | 5 | 1.80 | 1.60 | 1.00 |
| | Dessication | 11 | 2.00 | 1.55* | 1.45* |
| | Flushing | 5 | 1.80 | 1.20 | 1.00 |
| | Erosion | 1 | 2.00 | 1.00 | 1.00 |
| | Desquamation | 2 | 1.00 | 1.00 | 1.00 |
| | Papula | 2 | 1.00 | 1.50 | 1.00 |
| | Vesicle | 1 | 1.00 | 1.00 | 2.00 |
| General observation | | 11 | 1.64 | 1.18 | 1.27 |

Wilcoxon test: *: $p < 0.05$, **: $p < 0.01$

As shown in Table 3, with respect to the symptoms of face, in the NAG group, effects for significant improvements were recognized in the items of "dessication", "flushing" and "spread of cosmetics". On the other hand, in the placebo group, no significance was recognized in any item of observation. Further, in the symptom of whole body, significant improvements were recognized in the item of "dessication" in both groups. In the general observation, although significant improvements were recognized in the NAG group, no significant improvement was recognized in the placebo group.

(2) Moisture Content, Oil and Fat Content, and Acidity (pH)

The moisture content was measured by using Corneometer CM825 (manufactured by Courage+Khazaka Electronic Gmbh). This apparatus measures the moisture content of epidermis by measuring the electrostatic capacity via corneal layer, and is known to be less in error as compared with a conventional impedance method or infrared spectrophotometric method.

The oil and fat content was measured by using Sebumeter SM810 (manufactured by Courage+Khazaka Electronic Gmbh). In use of this apparatus, a special tape which absorbs only the oil and fat content is attached to the measurement site for 30 seconds and the oil and fat content is measured by the change of light transmittance of the tape. This apparatus is known not to be affected by humidity, etc.

The acidity was measured by using PH 900 (manufactured by Courage+Khazaka Electronic Gmbh). In use of this apparatus, an electrode is contacted to a skin surface through an ion-permeable membrane neighboring to a glass membrane and the acidity can be measured without electrochemical invasion. In this connection, the optimum pH of female's skin is about 5.5.

Measurement sites were 1 cm below the left eye, medial part of left upper arm (3 cm above the elbow), and poll (3 cm below spinous process of neck). With respect to the oil and fat content, since most subjects were scored at 0 at the left upper arm and the poll, only the site below the left eye was measured from the 2nd inspection.

In order to keep the environments for the measurements as equal as possible, a room having its internal conditions adjusted to be constant was prepared before the measurements (room temperature: 18 to 20° C., humidity: 45 to 60%), and the subjects were asked to keep in rest in this room for at least 30 minutes. Further, with respect to the makeup at the measurement site, it was in principle prohibited to put on makeup from 60 minutes before the inspection.

The results are shown in Table 4.

TABLE 4

| | | Before ingestion | After 4 weeks | After 8 weeks |
|---|---|---|---|---|
| | | NAG group (n = 11) | | |
| Moisture content | Below left eye | 48.0 ± 8.8 | 58.8 ± 14.2* | 56.2 ± 8.4** |
| | Left upper arm | 37.8 ± 7.8 | 38.7 ± 5.8 | 36.2 ± 6.8 |
| | Poll | 51.3 ± 5.6 | 51.9 ± 5.4 | 52.1 ± 10.9 |
| Acidity (pH) | Below left eye | 6.0 ± 1.0 | 5.7 ± 0.5 | 5.8 ± 0.4 |
| | Left upper arm | 5.5 ± 0.3 | 5.6 ± 0.3 | 5.7 ± 0.4 |
| | Poll | 5.7 ± 1.1 | 5.4 ± 0.3 | 5.3 ± 0.4 |
| Oil and fat content | Below left eye | 63.8 ± 42.3 | 53.0 ± 29.2 | 40.8 ± 18.7* |
| | | Placebo group (n = 11) | | |
| Moisture content | Below left eye | 58.6 ± 11.7 | 57.8 ± 10.4 | 48.1 ± 10.2* |
| | Left upper arm | 37.6 ± 9.5 | 36.5 ± 6.7 | 32.2 ± 8.5 |
| | Poll | 51.7 ± 18.9 | 49.2 ± 14.1 | 53.6 ± 20.8 |
| Acidity (pH) | Below left eye | 5.7 ± 0.6 | 5.7 ± 0.5 | 5.8 ± 0.5 |
| | Left upper arm | 5.4 ± 0.4 | 5.7 ± 0.4* | 5.6 ± 0.5 |
| | Poll | 5.7 ± 0.7 | 5.5 ± 0.4 | 5.6 ± 0.4 |
| Oil and fat content | Below left eye | 37.1 ± 32.2 | 30.1 ± 20.3 | 42.6 ± 30.1 |

Wilcoxon test: *p < 0.05, **p < 0.01

As shown in Table 4, significant increase was confirmed in the moisture content at the site below the left eye in the NAG group. Further, significant decrease in the oil and fat content was confirmed. On the other hand, in the placebo group, significant decrease was recognized in the moisture content at the site below the left eye.

(3) Analysis by a Microscopic Three-dimensional Skin Surface Analyzer (VISIOSCAN)

This analysis was conducted by using a digital analyzer of the skin surface (VISIONSCAN: manufactured by Courage+Khazaka Electronic Gmbh). In use of this apparatus, the skin surface was irradiated with special ultraviolet ray source, and the image is taken by a high performance CCD camera and digitalized for evaluation. The following factors were sampled as parameters.

(a) SEsm (Skin Smoothness)

This value is calculated from the average of the width and depth of wrinkles by the following formula (i), and one of indices which show the smoothness of skin. The smaller this value is, the smoother the skin surface is.

$$SEsm = (Co - Cu) \times (Fmx - Fmy) \times K \quad \text{(i)}$$

Fmx: average width of furrows for the row analysis.
Fmy: average width of furrows for the column analysis.
Co: right frontier of the histogram whose calculation is based on a set-up values.
Cu: left frontier of the histogram whose calculation is based on a set-up values.
K: factor (b) SEr (Skin Roughness)

This value is obtained by calculating the ratio of points darker than the set-up points in the whole image and further calculating by the following formula (ii), and one of indices which show the roughness of skin. The higher the value is, the rougher the skin is.

$$SEr = I/(Nx \times Ny) \times 100 \quad \text{(ii)}$$

I: counter whose start value is 0 and which is incremented each time the gray value of the current point is smaller than the threshold issued from the set-up programs.
Nx: amount of point per row.
Ny: amount of point per column.

(c) SEsc (Skin Scaliness)

Epidermolysis parts are counted to be brighter than the set-up values in the image. The SEsc value is obtained by calculating the ratio of these parts relative to the entire part by the following formula (iii), and is one of indices which show the dryness of scale (corneum). The lower the value is, the more moist and the less epidermolysis (scale).

$$SEsc = I/(Nx \times Ny) \times 100 \quad \text{(iii)}$$

I: counter whose start value is 0 and which is incremented each time the gray value of the current point is bigger than the threshold issued from the set-up programs.
Nx: amount of point per row.
Ny: amount of point per column.

(d) SEw (Skin Wrinkles)

This value is an index which is calculated by the following formula (iv) and shows the surface texture in vertical and horizontal directions of skin or the number and width of wrinkles. The higher the value is, the more the number of wrinkle is and the wider the width of wrinkles is.

$$SEw = Fmx \times Fmy/(Fax \times Fay) \times Fay/Fax \times K \quad \text{(iv)}$$

Fax: amount of furrows for the row analysis.
Fmx: average width of furrows for the row analysis.
Fay: amount of furrows for the column analysis.
Fmy: average width of furrows for the column analysis.
K: factor (e) Correction K (Kurtosis)

This value shows the smoothness of the whole skin. This value shows the quality of histogram in hue point of skin. The closer to 0 the value is, the smoother in curve the hue point is and the closer to ideal skin. The results of the above tests (a) to (e) are shown in Table 5.

TABLE 5

| | | Before ingestion | After 4 weeks | After 8 weeks |
|---|---|---|---|---|
| | | NAG group (n = 11) | | |
| Kurtosis (Ideal value: 0) | Below left eye | 0.58 | 0.34 | 0.30 |
| | Left upper arm | 0.97 | 0.40 | 0.50 |
| | Poll | 0.79 | 0.39 | 0.39 |
| SEsm (Ideal value: Lowest value) | Below left eye | 378.1 | 337.6 | 309.4 |
| | Left upper arm | 384.7 | 324.7 | 379.9 |
| | Poll | 443.8 | 338.9* | 345.2* |
| SEr (Ideal value: Lowest value) | Below left eye | 0.25 | 0.26 | 0.21 |
| | Left upper arm | 0.30 | 0.22 | 0.28 |
| | Poll | 0.51 | 0.32 | 0.40 |
| SEsc (Ideal value: Lowest value) | Below left eye | 238.4 | 137.0 | 133.0 |
| | Left upper arm | 342.9 | 195.8 | 202.4 |
| | Poll | 352.4 | 201.6 | 169.3* |
| SWw (Ideal value: Lowest value) | Below left eye | 33.2 | 29.0 | 27.8 |
| | Left upper arm | 30.2 | 26.4 | 31.9 |
| | Poll | 27.3 | 23.4 | 29.5 |
| | | Placebo group (n = 11) | | |
| Kurtosis (Ideal value: 0) | Below left eye | 0.42 | 0.76* | 0.30 |
| | Left upper arm | 0.43 | 0.59 | 0.42 |
| | Poll | 0.58 | 0.53 | 0.43 |
| SEsm (Ideal value: Low- | Below left eye | 379.6 | 398.8 | 353.7 |
| | Left upper arm | 335.7 | 373.1 | 335.1 |

TABLE 5-continued

|  |  | Before ingestion | After 4 weeks | After 8 weeks |
|---|---|---|---|---|
| est value) | Poll | 378.2 | 414.1 | 366.2 |
| SEr (Ideal | Below left eye | 0.24 | 0.23 | 0.24 |
| value: Low- | Left upper arm | 0.10 | 2.51 | 0.22 |
| est value) | Poll | 0.35 | 0.33 | 0.44 |
| SEsc (Ideal | Below left eye | 166.8 | 146.7 | 158.0 |
| value: Low- | Left upper arm | 214.1 | 256.1 | 246.5 |
| est value) | Poll | 231.8 | 219.7 | 202.2 |
| SEw (Ideal | Below left eye | 29.8 | 33.6 | 33.7 |
| value: Low- | Left upper arm | 23.7 | 28.1 | 24.4 |
| est value) | Poll | 27.5 | 26.0 | 29.3 |

Wilcoxon test: *$p < 0.05$

As shown in Table 5, in the NAG group, significant decrease was confirmed in the SEsm value and the SEsc value at the poll, whereby it was found that the smoothness of skin was recovered, the dryness of corneum was reduced and the scale was decreased. On the other hand, in the placebo group, no significant decrease was confirmed in every value.

EXAMPLE 1

Respective materials as indicated in Table 6 were mixed and granulated by a fluidized bed granulator, and then triangle tablets of 300 mg/tablet were formed by a tabletting machine (NAG content: 120 mg/tablet). The tabletting property was excellent.

TABLE 6

| NAG | 40 wt % |
|---|---|
| Collagen | 30 wt % |
| Lactose | 15 wt % |
| Cellulose powder | 10 wt % |
| Citric acid | 2 wt % |
| Perfume | 2 wt % |
| Sucrose fatty ester | 1 wt % |
| Total | 100 wt % |

EXAMPLE 2

Respective materials were kneaded so that the incorporated amounts per capsule (300 mg/capsule) would be as indicated in the following Table 7, and triangle soft capsules were prepared by a soft capsule filling machine by using gelatin as an encapsulating agent. The filling property was excellent.

TABLE 7

| NAG | 30 mg |
|---|---|
| Vitamin E | 50 mg |
| Soybean lecithin | 20 mg |
| Safflower oil | 170 mg |
| Vitamin C | 20 mg |
| Glycerol fatty ester | 5 mg |
| Beeswax | 5 mg |
| Total | 300 mg/tablet |

EXAMPLE 3

Respective materials were mixed in the proportion as indicated in Table 8 and granulation was carried out using a 0.5% guar gum solution as a binder by a fluidized bed granulator, to obtain 9.7 kg of NAG-containing granules. No moisture absorption of NAG was observed, dispersion of powder was good, and uniform granules were prepared.

TABLE 8

| NAG | 1.5 kg |
|---|---|
| Calcined cow bone powder | 0.8 kg |
| Chondroitin sulfate | 0.3 kg |
| Vitamin C | 0.1 kg |
| Vitamin B mixture | 0.1 kg |
| Glucose | 2.1 kg |
| Dextrin | 3.5 kg |
| Citric acid | 0.4 kg |
| Lemon fruit juice powder | 1.2 kg |
| Total | 10.0 kg |

EXAMPLE 4

All of respective materials were dissolved in water in the proportion as indicated in the following Table 9 to prepare a paste-like sample.

This product was stable even after cold atorage for one year.

TABLE 9

| NAG | 30 g |
|---|---|
| Blue berry extract | 100 g |
| Citric acid | 10 g |
| White refined sugar | 50 g |
| Pectin | 1 g |
| Perfume | 0.2 g |
| Water | 109 g |
| Total | 300.2 g |

EXAMPLE 5

Candy

Candy was prepared in accordance with a conventional method in the proportion as indicated in the following Table 10.

This candy could be prepared by usual steps without causing browning due to the addition of NAG.

TABLE 10

| NAG | 20 wt % |
|---|---|
| Sugar | 36 wt % |
| Starch syrup | 40 wt % |
| Fruit juice | 3 wt % |
| Acidifier | 0.5 wt % |
| Coloring matter, Perfume | 0.5 wt % |
| Total | 100 wt % |

EXAMPLE 6

Gummi

Gummi was prepared in accordance with a conventional method in the proportion as indicated in the following Table 11. The production of gummi includes a step of heating for evaporation of water after a step of mixing respective starting materials. Accordingly, in Table 11, the finished amount is less than the total of respective materials.

TABLE 11

| | |
|---|---|
| NAG | 200 g |
| Granulated sugar | 170 g |
| Starch syrup | 260 g |
| Sorbitol | 180 g |
| Citric acid | 2 g |
| Coloring matter, Perfume | 0.5 g |
| Gelling agent | 80 g |
| Water | 200 g |
| Finished amount | 1,000 g |

EXAMPLE 7

Cookie

Cookie was prepared in accordance with a conventional method in the proportion as indicated in the following Table 12.

This cookie could be prepared by usual steps without causing browning due to the addition of NAG.

TABLE 12

| | |
|---|---|
| NAG | 80 g |
| Unsalted butter | 120 g |
| Sugar | 60 g |
| Egg | 20 g |
| Weak flour | 180 g |
| Baking powder | 1 g |
| Cocoa | 20 g |
| Milk | 10 g |

EXAMPLE 8

Jelly

Jelly was prepared in accordance with a conventional method in the proportion as indicated in the following Table 13. The production of jelly includes a step of heating for evaporation of water after a step of mixing respective starting materials. Accordingly, in Table 13, the finished amount is less than the water amount mixed with the starting materials.

TABLE 13

| | |
|---|---|
| NAG | 100 g |
| Gelling agent | 3.5 g |
| Sugar | 50 g |
| Fruit juice | 10 g |
| Perfume, Coloring matter | Proper quantity |
| Acidifier, Sweetener | Proper quantity |
| Water | 1,000 ml |
| Finished amount | 750 ml |

EXAMPLE 9

Powdered Soup

Powdered soup was prepared in accordance with a conventional method in the proportion as indicated in the following Table 14.

This powdered soup was soluble in hot water readily, and its taste was good.

TABLE 14

| | |
|---|---|
| NAG | 4 g |
| Chicken consommé | 0.5 g |
| Dehydrated seaweed (Wakame) | 0.4 g |
| Sesame oil | 0.1 g |
| | 150 ml of hot water/meal |

EXAMPLE 10

Refreshing Drink

Refreshing drink was prepared in accordance with a conventional method in the proportion as indicated in the following Table 15.

TABLE 15

| | |
|---|---|
| NAG | 1,000 mg |
| Collagen | 100 mg |
| Ca lactate | 1,000 mg |
| $MgCl_2$ | 50 mg |
| Mixture of vitamins | 60 mg |
| Acidifier, Perfume | Proper quantity |
| Sucrose, Glucose, Liquid sugar | Proper quantity |
| Preserver | Proper quantity |
| | 50 ml/bottle |

EXAMPLE 11

Tablet

Tablet was prepared in accordance with a conventional method in the proportion as indicated in the following Table 16.

TABLE 16

| | |
|---|---|
| NAG | 80.0 wt % |
| Chitinoligosaccharide | 10.0 wt % |
| Mixture of vitamins | 0.5 wt % |
| Perfume | 0.5 wt % |
| Sucrose fatty acid | 3.0 wt % |
| Maltitol | 6.0 wt % |
| Total | 100 wt % |

EXAMPLE 12

Candy

Candy was prepared in accordance with a conventional method in the proportion as indicated in the following Table 17.

TABLE 17

| | |
|---|---|
| Sugar | 47.7 wt % |
| Reduced malt sugar syrup (water content: 25%) | 40.0 wt % |
| NAG | 15.0 wt % |
| Chitinoligosaccharide | 5.0 wt % |
| Citric acid | 2.0 wt % |
| Perfume | 0.3 wt % |
| Total (solid state) | 100 wt % |

EXAMPLE 13

Beverage

Beverage was prepared in accordance with a conventional method in the proportion as indicated in the following Table 18.

TABLE 18

| | |
|---|---|
| Collagen peptide | 6.0 wt % |
| NAG | 2.0 wt % |
| Vitamin C | 0.6 wt % |
| Vitamin B$_2$ | 0.01 wt % |
| Erythritol | 10.0 wt % |
| Acidifier | 1.2 wt % |
| Sweetener | Small quantity |
| Perfume | Small quantity |
| Purified water | Proper quantity |
| Total | 100.0 wt % |

EXAMPLE 14

Powdered Soup

Powdered soup was prepared in accordance with a conventional method in the proportion as indicated in the following Table 19.

TABLE 19

| | |
|---|---|
| NAG | 10.0 wt % |
| Collagen peptide | 30.0 wt % |
| Chicken consommé | 40.0 wt % |
| Sesame oil | 2.0 wt % |
| Dehydrated seaweed (Wakame) | 8.0 wt % |
| Dextrine | 10.0 wt % |
| Total | 100.0 wt % |

As described above, according to the present invention, by orally ingesting the natural-type NAG, NAG is rapidly absorbed and transferred to skin layer, and then becomes a starting material of hyaluronic acid or the like, by which the moisture and tension of skin can be improved and the rough skin and fine wrinkles can be prevented or ameliorated. Further, the natural-type NAG has no risk such that a solvent or the like remains, and it is safe for human bodies and can be ingested without risk.

What is claimed is:

1. A method for promoting amelioration of rough skin and wrinkles in a human which comprises orally administering to said human an effective amount of a skin care agent to improve moisture and tension of the skin comprising:
   (a) a collagen peptide that is obtained by extracting collagen from fish skin or fish bone, and producing a mixture of collagen peptides by enzymolysis, the collagen peptide having a number average molecular weight of 1,000 to 10,000; and
   (b) N-acetylglucosamine;
   wherein the collagen peptide is contained in an amount of from 0.1 to 99.9% by weight of the total weight of the skin care agent and the N-acetylglucosamine is contained in an amount of from 0.1 to 99.9% by weight of the total weight of the skin care agent.

2. The method for promoting amelioration of rough skin and wrinkles according to claim 1, wherein the mixture of collagen peptides is prepared by carrying out a reverse osmosis membrane treatment after the enzymolysis, such that said collagen peptide contains at most 1.0% by weight of free amino acid and at most 2 ppm of arsenic, as measured by HPLC.

3. The method for promoting amelioration of rough skin and wrinkles according to claim 1, wherein the skin care agent further comprises an ingestible carrier.

4. The method for promoting amelioration of rough skin and wrinkles according to claim 3, wherein the ingestible carrier is at least one food selected from the group consisting of confectioneries, powdered soups, dairy products, beverages, gum, candies, tabletted confectioneries, chocolate, jelly, cookies, corn potage soup, consomme soup, milk, pudding, yogurt, ice cream, alcohol beverages, vitamin beverages, mineral beverages, coffee beverages and nutrition drinks.

5. The method for promoting amelioration of rough skin and wrinkles according to claim 1, wherein the skin care agent is administered in the form of tablets, capsules, a powder, granules, a liquid or a paste.

6. The method for promoting amelioration of rough skin and wrinkles according to claim 1, wherein the N-acetylglucosamine is contained in an amount of from 1 to 50% by weight of the total weight of the skin care agent.

7. The method for promoting amelioration of rough skin and wrinkles according to claim 1, wherein the N-acetylglucosamine is orally administered in an amount of from 0.1 to 15 g per day.

8. The method for promoting amelioration of rough skin and wrinkles according to claim 1, wherein the N-acetylglucosamine is obtained by hydrolysis of chitin with an acid, an enzyme or an acid and an enzyme.

9. The method for promoting amelioration of rough skin and wrinkles according to claim 1, wherein the N-acetylglucosamine is contained in an amount of from 35 to 50% by weight of the total weight of the skin care agent.

10. The method for promoting amelioration of rough skin and wrinkles according to claim 1, wherein N-acetylglucosamine is contained in a mixture with chitinoligosaccharide, said chitinoligosaccharide being produced when the N-acetylglucosamine is obtained by hydrolysis of chitin; and said chitinoligosaccharide being contained in an amount of from 0.1 to 20% by weight of the total weight of the skin care agent.

11. The method for promoting amelioration of rough skin and wrinkles according to claim 10, wherein the mixture of collagen peptides is prepared by carrying out a reverse osmosis membrane treatment after the enzymolysis, such that said collagen peptide contains at most 1.0% by weight of free amino acid and at most 2 ppm of arsenic, as measured by HPLC.

12. The method for promoting amelioration of rough skin and wrinkles according to claim 2, wherein the reverse osmosis membrane treatment is performed with a reverse osmosis membrane having a salt-preventing rate of 10%.

13. The method for promoting amelioration of rough skin and wrinkles according to claim 11, wherein the reverse osmosis membrane treatment is performed with a reverse osmosis membrane having a salt-preventing rate of 10%.

* * * * *